United States Patent
Desroches et al.

(10) Patent No.: US 11,497,384 B2
(45) Date of Patent: Nov. 15, 2022

(54) OPTICAL FIBRE WITH A FUNCTIONALISED EXPLORATION END

(71) Applicants: KAMAX INNOVATIVE SYSTEM, Limoges (FR); CENTRE NATIONAL DE LA RECHERCHE SCIENTIFIQUE, Paris (FR); UNIVERSITÉ DE LIMOGES, Limoges (FR)

(72) Inventors: Jérôme Desroches, Couzeix (FR); Olivier Baudet, Limoges (FR); Martine Lejeune, Limoges (FR); Romain Trihan, Beaupuy (FR); Fabrice Lalloue, Isle (FR)

(73) Assignees: KAMAX INNOVATIVE SYSTEM, Limoges (FR); CENTRE NATIONAL DE LA RECHERCHE SCIENTIFIQUE, Paris (FR); UNIVERSITÉ DE LIMOGES, Limoges (FR)

( * ) Notice: Subject to any disclaimer, the term of this patent is extended or adjusted under 35 U.S.C. 154(b) by 223 days.

(21) Appl. No.: 16/613,695

(22) PCT Filed: May 15, 2018

(86) PCT No.: PCT/FR2018/051170
§ 371 (c)(1),
(2) Date: Nov. 14, 2019

(87) PCT Pub. No.: WO2018/211210
PCT Pub. Date: Nov. 22, 2018

(65) Prior Publication Data
US 2020/0288943 A1   Sep. 17, 2020

(30) Foreign Application Priority Data
May 15, 2017 (FR) ....................... 1770494

(51) Int. Cl.
*G02B 6/36* (2006.01)
*A61B 1/00* (2006.01)
*G02B 23/26* (2006.01)

(52) U.S. Cl.
CPC ........ *A61B 1/0017* (2013.01); *A61B 1/00096* (2013.01); *A61B 1/00126* (2013.01); *G02B 6/3624* (2013.01); *G02B 23/26* (2013.01)

(58) Field of Classification Search
None
See application file for complete search history.

(56) References Cited

U.S. PATENT DOCUMENTS 5,993,378 A * 11/1999 Lemelson ......... A61M 25/0069
                                                    600/109
2014/0275765 A1* 9/2014 Gebhart .................. G01J 3/453
                                                    600/103
(Continued)

FOREIGN PATENT DOCUMENTS

EP   2 777 482 A1   9/2014
JP   2011-072424 A  4/2011
(Continued)

OTHER PUBLICATIONS

International Search Report with English translation and Written Opinion with Machine translation dated Aug. 28, 2018 in corresponding International Application No. PCT/FR2018/051170; 13 pages.

*Primary Examiner* — Chad H Smith
(74) *Attorney, Agent, or Firm* — Maier & Maier, PLLC

(57) ABSTRACT

An optical fibre having a functionalised distal exploration end including a sheath, and a ferrule rigidly connected to the sheath at the distal exploration end, characterised in that the
(Continued)

distal exploration end has a functionalised head which is removably attached on the ferrule. Also, a method of assembling the optical fibre.

2 Claims, 1 Drawing Sheet

(56) References Cited

U.S. PATENT DOCUMENTS

2014/0340926 A1* 11/2014 Komukai ............. A61B 1/0011
  362/553
2016/0296104 A1* 10/2016 Smith ................ A61B 1/00096

FOREIGN PATENT DOCUMENTS

WO    2003/051184 A1    6/2003
WO    2016/184014 A1    11/2016

* cited by examiner

OPTICAL FIBRE WITH A FUNCTIONALISED EXPLORATION END

FIELD

The invention concerns the technical field of optical fibres, in particular functionalised optical fibres. More particularly, the invention concerns an optical fibre with a functionalised exploration end.

BACKGROUND

The invention will be more particularly described with regard to a medical use employing a catheter or an endoscope, without however being limited to this. In the medical field, endoscopy makes it possible to examine the inside of a cavity using a backscattered light detection technique, employing one or more optical fibres. In known manner, an endoscope comprises a flexible envelope housing one or more optical fibres, and the downstream distal end of which comprises a probe connected to the optical fibres and intended to be introduced into the cavity to be examined, and the upstream distal end opposite the probe is intended to be connected to a light source aligned with the one or more optical fibres in order to transmit light to the probe and into the cavity, light detectors also arranged in alignment with the optical fibres and at the upstream end being intended for receiving the backscattered light from the inside of the cavity and transmitted back via the fibres. The backscattered and detected light is then processed and analysed.

SUMMARY

In known manner, an optical fibre comprises a sheath surrounding one or more fibre cores, and its distal end intended for exploration is in the form of a rigid ferrule firmly secured to the end of the sheath of the fibre, and the outer face of which, transverse to the axis of the fibre, is transparent. The ferrule is made, for example, from transparent epoxy resin that has been overmoulded onto the sheath of the fibre.

Depending on the intended use, the exploration end of the fibre may also comprise functional elements suitable for the type of detection. For example, an exploration end of a functionalised fibre is known which is equipped with mesoporous silica micropads associated with ligands capable of interacting with biomarkers overexpressed on tumour cells; such an optical fibre can be used to detect cancer cells. The functional end of an optical fibre can also be functionalised by photosensitisers in order to destroy cancer cells by dynamic phototherapy (a method known as DPT).

However, currently, a practitioner during the course of a given operation or successive operations, may have need of a large number of specific optical fibres, the functional ends of which are dedicated to a particular use or are disposable.

Thus, the plurality of applications or the need for disposable functionalised ends implies having available a large number of optical fibres with specific functionality, which creates a non-negligible volume and bulk in an operating theatre.

Therefore, the invention aims in particular to overcome the above-mentioned disadvantage by providing a solution which simplifies the quantity and management of optical fibres before being made available, whatever the intended application, while providing quick and easy implementation for the practitioner.

A first object of the invention is a removable functionalised exploration head comprising means for fitting on an optical fibre. A second object of the invention is an optical fibre on which a removable exploration head is fitted. A third object of the invention is a kit comprising an optical fibre and one or more sets of exploration heads, identically functionalised or having varied functions.

The invention has many advantages and, in particular, that of allowing a differentiated storage of the optical fibre and the exploration heads. Indeed, each exploration head may require specific storage conditions (control of the exposure to air and/or light, temperature control, humidity control, etc.), for example when it is functionalised with proteins or ligands sensitive to gases, light, temperature or humidity. By contrast, the optical fibre itself can be stored in a simpler and more practical manner. The same applies to the sterilisation conditions: through the invention these can be different and suitable for the optical fibre on the one hand and for each exploration head on the other hand.

It is also recognised that it is difficult to print functionalised heads on optical fibres that are several metres long. This problem is solved by the invention.

Yet more importantly, when the head is functionalised with ligands capable of identifying cancerous tissues, the functionalised head can be changed after each contact in order to avoid any undesirable propagation of cancerous tissues in the organism.

The invention also relates to a solution for managing the treatment of the medical waste that is constituted by an optical fibre with a used functionalised head; the heads can be thrown away, while the fibres are generally sterilised and reused.

Finally, the use of a removable functionalised head enables optical optimisation of the fibre with functionalised head.

According to the invention, the optical fibre having a functionalised distal exploration end comprises a sheath and a ferrule rigidly connected to the sheath at the distal exploration end, and is characterised in that the distal exploration end has a functionalised head which is removably attached to the ferrule.

According to an embodiment, the functionalised head is connected subsequently, when an ordinary optical fibre is made available to a practitioner and before the operation. "Ordinary optical fibre" means a fibre which is not equipped with a functionalised tip, but only comprising the sheath of the optical fibre surrounding one or more cores, and an end ferrule to rigidify the end of the fibre in view of its use.

The "functionalised head" is the part of the fibre playing the role of probe or, more generally, any technical function using light emitted at the end of the optical fibre in order to cooperate or interact with the environment into which the end of the fibre is introduced. The ferrule of the optical fibre of the invention has only the function of a mechanical attachment means for the functionalised head.

Thus, it suffices to have just a few (ordinary) optical fibres in the operating theatre while having available a large number of functionalised heads, which have a very small bulk; the practitioner will have only to choose the head or heads which he needs for his operation and associate them with one or more optical fibres depending on the use. The quantity of optical fibres made available in an operating theatre is then greatly reduced, while guaranteeing that the practitioner benefits from all the functionalities of which he will need for the various uses through the removable heads, each having a dedicated functionality.

According to one feature, the ferrule and the functionalised head are rigidly attached by mechanical assembly, such as by crimping, fastening, screwing, clipping, twist locking.

The attachment of the functionalised head to the ferrule is designed such that the head and the ferrule cannot separate during use, in particular when the fibre has been introduced into the body of a patient.

In an embodiment, the ferrule and the functionalised head respectively comprise attachment means by mutual interaction, such as male and female interaction means.

Advantageously, the functionalised head has an outer face, called emission face, at least one portion of which is transparent and intended to be facing the core or cores of the optical fibre for the passage of light. Preferably, the transparent portion of the outer face has no surface roughness; for example, it is polished.

The functionalised head comprises a hollow body, the inner space of which houses the ferrule.

In an embodiment, the functionalised head comprises a hollow body, preferably limited by a cylindrical wall, and has an outer face transverse to the wall at least a portion of which forms a passage for light, and attachment means arranged on the cylindrical wall or on the end face opposite the face provided for the passage of the light.

The functionalised head has a body made of polymer material or of glass, or is ceramic-based, stainless steel based or composite material based, or is made of a combination of several materials, the outer emission face of the head intended to be facing the fibre core or cores being made of material that is transparent to light.

The functionalised head has a cylindrical body which can be of diameter between 0.5 and 5 mm, preferably approximately 1 to 3 mm. The length of the cylindrical body can be from 10 to 500 mm, preferably approximately 20 mm. In the context of the present invention, the term "approximately" placed before a figure signifies plus or minus 20% of the value of this figure.

The functionalised head comprises functional elements contributing at least one technical function to the optical fibre, such as mesoporous silica micropads or other anchoring means for associating ligands there that are suitable for the detection of cancer cells, or photosensitiser ligands for the destruction of cancer cells by phototherapy.

The invention also relates to a functionalised head having the above features and suitable for being removably connected to an optical fibre and assembled to it.

The invention also relates to a kit for a functionalised optical fibre comprising at least one functionalised head as described above, the kit being able to include a plurality of identical or different functionalised heads each of the heads being removably attachable to an optical fibre.

The invention also relates to the use of at least one optical fibre with functionalised head of the invention in endoscopy Of course, by adapting the function of the functionalised head, the fibre of the invention can be applied to any type of exploration.

The invention also relates to a device for packaging a functionalised head according to the invention, the head comprising attachment means intended for its assembly to an optical fibre, characterised in that the device comprises a shell that houses the head except for the attachment means, and a cover removably attached to the shell and capping said attachment means.

Finally, the invention relates to a method for assembling an optical fibre with a functionalised head of the invention using the device for packaging said head. The head is delivered to the user in its packaging device (packaging).

The assembly method consists of removing the cover from the packaging device, thus rendering the attachment means accessible, introducing (in particular by pushing when the attachment means are clipping means) the ferrule of the optical fibre into the functionalised head which is hollow, and separating the shell from the head; the head is then assembled on the fibre which is ready to use.

BRIEF DESCRIPTION OF THE FIGURES

The present invention is now described with the help of embodiments, which are for illustration only and do not limit the scope of the invention, and based on the attached illustrations, in which:

DETAILED DESCRIPTION

Figure 1:
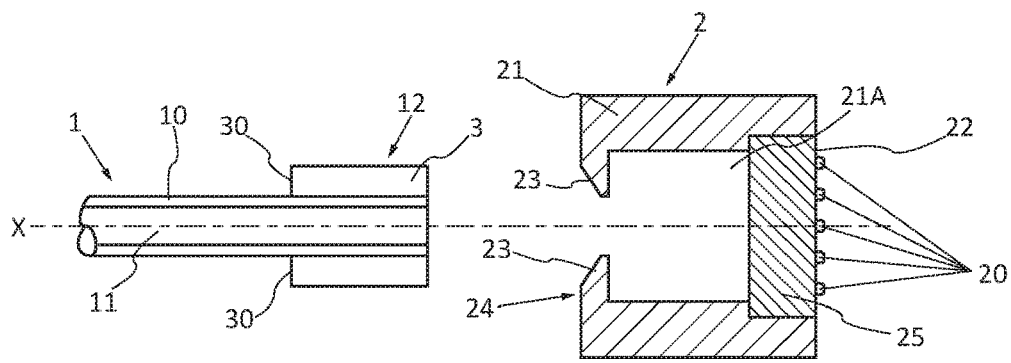
Figure 2:
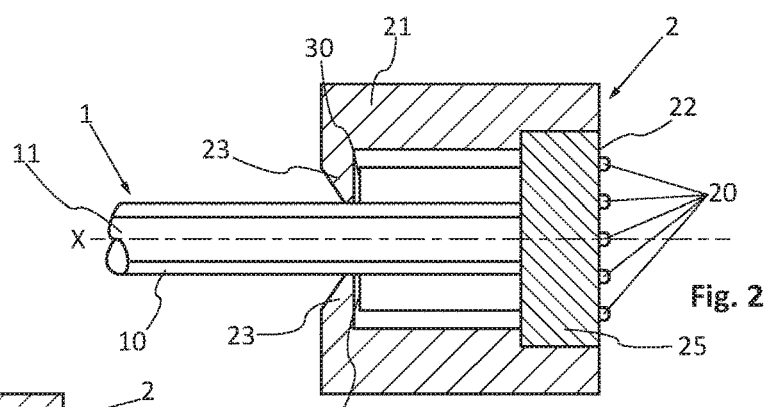
Figure 3:
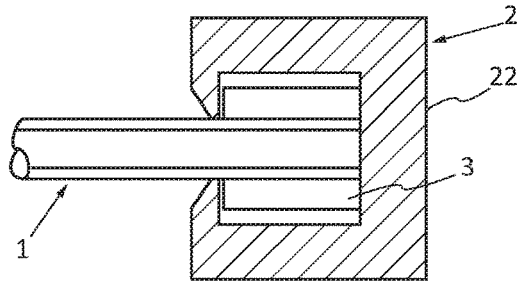
Figure 4:
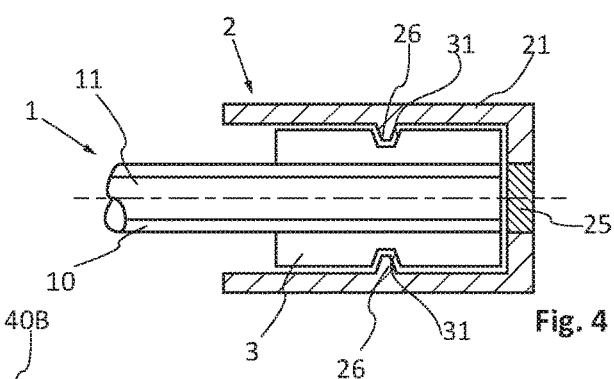
Figure 5:
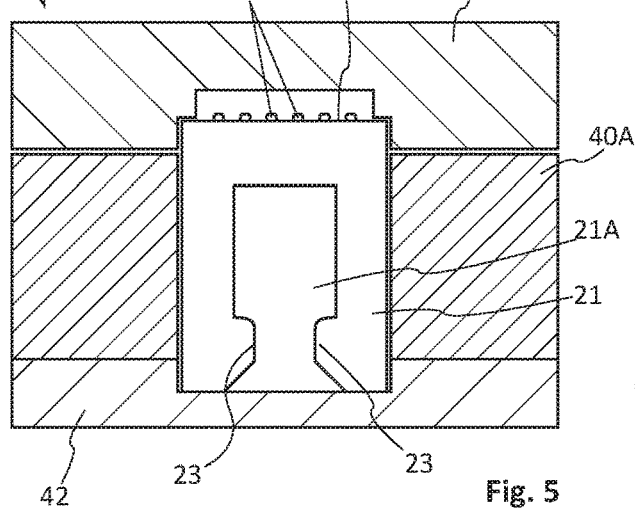
Figure 6:
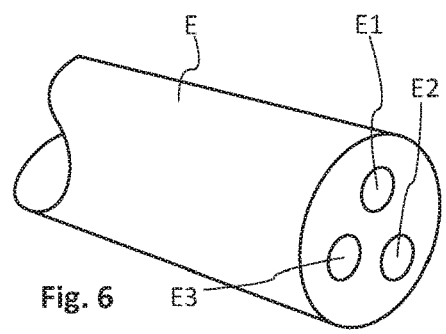

FIG. 1 shows a sectional view according to the invention of an optical fibre and of a functionalised head to be removably connected according to the invention, on the end of the optical fibre;

FIG. 2 corresponds to FIG. 1, the functionalised head being connected and assembled on the optical fibre;

FIGS. 3 and 4 are sectional views of variants of functional heads according to the invention each assembled at the end of an optical fibre;

FIG. 5 is a sectional view of the packaging device according to the invention for a removable functionalised head of the invention for ensuring its assembly at the end of an optical fibre; and FIG. 6 shows a partial schematic view, in perspective, of an endoscope comprising three channels, one channel of which is intended to house the optical fibre with functionalised head according to the invention.

The optical fibre 1 of the invention illustrated in FIGS. 1 to 4 comprises a functionalised exploration head 2 which is intended to be removably connected to the body of the optical fibre.

The optical fibre 1 equipped with its functionalised head 2 is used, for example, in an endoscope E, such as that schematically illustrated in FIG. 5. The endoscope example schematically illustrated in FIG. 6 comprises three channels E1, E2 and E3, intended to respectively house a light source, a camera and an optical fibre with functionalised head of the invention. The dimensions of the functionalised head and of the fibre can vary depending on the type of endoscope used. Functionalised heads with different functions can be slid via the operative channel of the endoscope.

With regard to FIG. 1, the optical fibre 1 comprises a sheath 10 and at least one core 11 with longitudinal axis X; it has a downstream end (not illustrated here) which is intended to be connected in known manner to a light source and an opposite downstream 12, forming the exploration end of the optical fibre from which the light necessary for the exploration will be emitted into a cavity into which the fibre will be introduced.

The exploration end 12 of the optical fibre is equipped, in known manner, with a ferrule 3 forming a rigid tip pierced at its centre and in which the sheath 10 of the optical fibre is attached.

According to the invention, the functionalised exploration head 2 is removably connected to the optical fibre 1, and more particularly to the ferrule 3 of the optical fibre, by the practitioner just before use of the fibre, once the choice of head has been made depending on the type of use, in other words depending on the required function of the head. Hence, the practitioner has available a plurality of functionalised heads and chooses the head with the appropriate function for the intended application, independently of the optical fibre.

In contrast to the prior art which proposes an exploration head that is already attached to the optical fibre with a view to its use, the invention provides a functionalised exploration head 2 which is independent of the optical fibre 1 before use.

Advantageously, the invention also proposes, with regard to FIG. 5, a packaging for each functionalised head before use, this packaging also constituting a support device for ensuring the assembly of the optical fibre 1 to the functionalised head 2 in a quick and easy manner by the practitioner, as will be seen below.

The functionalised exploration head 2 has at least one technical function related to the use of the optical fibre. It thus comprises functional elements 20 which impart a technical function to the head 2 and consequently to the optical fibre. The functionalised exploration head 2 does not have the sole task of allowing the passage of light emitted by the optical fibre, but rather also to make the optical fibre 1 functional.

By way of a non-limiting example, an exploration head 2 may comprise mesoporous silica micropads 20 which are equipped with specific ligands suitable for reacting with biomarkers which the exploration head will encounter during its use, such as those placed in a cavity of the human body for detecting cancer cells by recognition of a light spectrum profile linked to the biomarkers. In another example, a functionalised head may comprise mesoporous silica micropads 20 which are equipped with photosensitiser ligands which enable the destruction of cancer cells by dynamic phototherapy.

The functionalised exploration head 2 comprises a hollow cylindrical body 21 with the same central longitudinal axis X in the assembled position of the head 2 on the body of the optical fibre 1, and a distal end outer face 22 which is transverse to the axis of the cylindrical body and from which the light leaving the core 11 of the optical fibre is intended to be emitted.

The hollow cylindrical body 21 is closed on its emission end face 22.

At least one portion of the emission end face 22 is transparent and intended to be arranged facing the core 11 of the optical fibre.

The functional elements 20 are in particular associated, secured to the emission end face 22.

The functionalised exploration head 2 is secured to the ferrule 3 by mechanical assembly.

The functionalised exploration head 2 preferably comprises attachment means 23 for its mechanical assembly, without tools, by mutual interaction with the ferrule 3.

The mechanical assembly of the head removably connected on the ferrule 3 can be carried out, for example, by crimping, without the body 21 of the head necessarily comprising attachment means per se. However, the method of assembly by crimping requires at least one tool.

In the illustrated examples, a mechanical assembly by mutual interaction without a tool is preferred, such as clipping.

In the present example, in FIGS. 1 to 3, the ferrule 3 comprises a smooth-walled cylindrical body, whereas the functionalised exploration head 2 comprises, as attachment means 23 by mutual interaction, lugs spaced apart and facing each other which extend in the plane of the outer face 24 opposite the light emission face 22. The lugs 23 form hooks which interact with the edge 30 of the free end of the wall of the cylindrical body of the ferrule 3. The lugs 23 play a role as stops with said edge 30, preventing any withdrawal of the ferrule 3, once it is housed in the inner space 21A of the hollow cylindrical body 21.

The functionalised head 2 has, for example, its cylindrical body made of stainless steel, and comprises on its outer emission face 22, a window 25 made of transparent material, such as glass, for passage of the light emitted by the fibre. In a variant, the window 25 is an optical lens.

In the variant of FIG. 3, the functionalised head is entirely made of glass, its outer emission face 22 thus being transparent.

FIG. 4 illustrates an embodiment of the mechanical assembly of the functionalised head 2 to the ferrule 3. The means for attachment by mutual interaction of the functionalised head 2 with the ferrule 3 comprises an annular rib 26 on the inside of the wall of the cylindrical body 21 of the head 2, and a circular groove 31 on the outside of the wall of the cylindrical body of the ferrule 3, the rib 26 interacting by engaging in the groove 31, locking the head 2 in position on the ferrule 3.

The dimensions of the functionalised head 2 are, for example of order 20 to 30 mm in length and 1 to 3 mm in diameter. Consequently, the quick assembly procedure may be delicate with an optical fibre generally of diameter 1 mm, especially when this operation is to be carried out by the practitioner very shortly before his operation. In order to ensure a quick and simple assembly, the invention also provides a packaging device 4, such as schematically illustrated in FIG. 5, for a functionalised head 2 to be removably connected to an optical fibre.

The packaging device 4 serves as a support means for the functionalised head 2 in order to hold it in position during the introduction of the optical fibre 1 into the inner space 21A of the head 2.

The packaging device 4 comprises, on the one hand, a shell 40 with a part 40A or two parts 40A and 40B which house the cylindrical body 21 and the outer emission face 22, while the attachment means 23 of the head are arranged outside of the shell 40, and on the other hand a cover 42 which caps the attachment means 23.

The part 40B of the shell 40 receiving at least the outer emission face 22 of the functionalised head 2 is designed, for example, equipped with a cavity, so as not to press directly on the outer emission face 22 which comprises the functional elements 20, in order to protect these functional elements.

The cover 42 is removably attached on the shell 40.

The shell may be in two removable parts 40A and 40B, because it may form the support of the head 2 during the procedure of depositing the functional elements 20. During the depositing procedure, the cylindrical body 21 and the head are wedged in the first part 40A and the cover 42 is assembled, while the second part 40B is not present, leaving the outer emission face 22 accessible for depositing the functional elements.

After depositing, the second part 40B of the shell is assembled to close the assembly of the packaging device 4.

The packaging device 4 thus protects the assembly of the functionalised head 2. When the practitioner chooses a functionalised head in order to assemble it on an optical fibre, he grips the packaging device with one hand, undoes the cover 42 of the shell 4 with the other hand, and captures the optical fibre by introducing the optical fibre 1 from the side of the ferrule 3 into the hollow inner space 21A of the head. The ferrule 3 is inserted by pushing, with a very gentle force, to elastically move apart the clipping lugs 23. Once the lugs 23 clasp the edge 30 of the ferrule, the assembly is finished and locked.

Consequently, the functionalised head 2 that is to be removably connected on an ordinary optical fibre according to the invention, enables the practitioner in particular to have a significant number of heads with a reduced bulk, without having to provide an equivalent quantity of optical fibres which, otherwise, would be previously fitted and take up a significant storage volume.

The invention claimed is:

1. A packaging device for packaging a functionalised head, the functionalised head comprising removable attachment means intended for its assembly to an optical fibre to form a device comprising:
    the optical fibre having:
        a functionalised distal exploration end comprising a sheath, and
        a ferrule rigidly connected to the sheath at the distal exploration end; and
    the functionalised head configured to be removably attached on the ferrule,
        wherein the functionalised head comprises anchoring means for associating ligands, or
        wherein the functionalised head is functionalised with proteins or ligands,
    wherein the packaging device comprises a shell housing the functionalised head except for the removable attachment means, and a cover removably attached to the shell and capping said removable attachment means.

2. A method for assembling a device, using a packaging device for packaging the functionalised head, the functionalised head comprising attachment means intended for its assembly to an optical fibre, wherein the device as assembled comprises:
    the optical fibre having:
        a distal exploration end comprising a sheath, and
        a ferrule rigidly connected to the sheath at the distal exploration end; and
    the functionalised head configured to be removably attached on the ferrule,
        wherein the functionalised head comprises anchoring means for associating ligands, or
        wherein the functionalised head is functionalised with proteins or ligands,
    wherein the packaging device comprises a shell housing the head except for the attachment means, and a cover removably attached to the shell and capping said attachment means,
    said method comprising:
        a step of removing the cover making the removable attachment means accessible,
        a step of introducing the ferrule of the optical fibre into the functionalised head which is hollow, and
        a step of separating the shell from the functionalised head.

* * * * *